(12) United States Patent
Jiasharete

(10) Patent No.: US 10,307,283 B2
(45) Date of Patent: Jun. 4, 2019

(54) THERAPEUTIC DEVICE FOR SLOWLY STRETCHING THREE-DIMENSIONAL HIP JOINT FOR REPOSITION MOVEMENT

(71) Applicant: Jielile Jiasharete, Urumqi (CN)

(72) Inventor: Jielile Jiasharete, Urumqi (CN)

( * ) Notice: Subject to any disclaimer, the term of this patent is extended or adjusted under 35 U.S.C. 154(b) by 352 days.

(21) Appl. No.: 15/263,164

(22) Filed: Sep. 12, 2016

(65) Prior Publication Data

US 2016/0374845 A1    Dec. 29, 2016

Related U.S. Application Data

(63) Continuation of application No. PCT/CN2015/000162, filed on Mar. 10, 2015.

(30) Foreign Application Priority Data

Mar. 11, 2014   (CN) .......................... 2014 1 0086136

(51) Int. Cl.
*A61F 5/00* (2006.01)
*A61F 5/01* (2006.01)
*A61H 1/02* (2006.01)

(52) U.S. Cl.
CPC .......... *A61F 5/0193* (2013.01); *A61H 1/0244* (2013.01); *A61H 2001/0248* (2013.01); (Continued)

(58) Field of Classification Search
CPC ............ A61F 5/0193; A61F 2005/0183; A61F 2005/0181
(Continued)

(56) References Cited

U.S. PATENT DOCUMENTS 3,274,997 A * 9/1966 Hewson, Jr. .......... A61F 5/0193
602/19
3,730,177 A * 5/1973 Thum ................... A61F 5/0193
602/24
(Continued)

FOREIGN PATENT DOCUMENTS

CN          2080831 U      7/1991
CN          2132500 Y      5/1993
(Continued)

OTHER PUBLICATIONS

International Search Report of corresponding International PCT Application No. PCT/CN2015/000162, dated Jun. 3, 2015.
(Continued)

*Primary Examiner* — Kim M Lewis
(74) *Attorney, Agent, or Firm* — J.C. Patents

(57) ABSTRACT

A therapeutic device for slowly stretching a three-dimensional hip joint for reposition movement, where a chest-abdomen fastener fixing band (2) is fixed to a back cover (1); a shoulder fastener suspension band (3) is fixed to the back cover (1) and the chest-abdomen fastener fixing band (2); a pair of wing-shaped supporting bars (5) is fixed to the back cover (1); a pair of limb fixing bars (6) is connected to telescopic ends of a pair of hip joint forward-backward movement adjusters (9), and the pair of hip joint forward-backward movement adjusters (9) are fixed to the back cover (1); upward-downward lifting chute screws (4) are connected to hooks of the pair of wing-shaped supporting bars (5) and the limb fixing bars (6); and an inward-outward telescopic screw (8) is connected between the pair of limb fixing bars (6) which are provided with limb fastener fixing bands (7).

8 Claims, 1 Drawing Sheet

(52) U.S. Cl.
CPC ............ *A61H 2201/0119* (2013.01); *A61H 2201/0192* (2013.01); *A61H 2201/149* (2013.01); *A61H 2201/164* (2013.01); *A61H 2201/1614* (2013.01); *A61H 2201/1619* (2013.01); *A61H 2201/1623* (2013.01); *A61H 2201/1652* (2013.01); *A61H 2201/1664* (2013.01); *A61H 2209/00* (2013.01)

(58) Field of Classification Search
USPC ............................................... 602/24
See application file for complete search history.

(56) References Cited

U.S. PATENT DOCUMENTS

| | | | | |
|---|---|---|---|---|
| 4,108,168 | A * | 8/1978 | Craig | A61F 5/0193 128/870 |
| 4,913,136 | A * | 4/1990 | Chong | A61F 5/0193 602/24 |
| 5,522,792 | A * | 6/1996 | Bassett | A61F 5/0193 5/601 |
| 6,254,561 | B1 * | 7/2001 | Borden | A61N 5/1049 128/845 |
| 6,540,703 | B1 | 4/2003 | Lerman | 602/5 |
| 8,545,424 | B2 * | 10/2013 | Hirata | A61F 5/0193 602/19 |
| 2009/0216165 | A1 * | 8/2009 | Christenhusz | A61F 5/0193 602/24 |
| 2012/0232451 | A1 | 9/2012 | Topinka | 602/19 |
| 2012/0259259 | A1 * | 10/2012 | Chugunov | A61F 5/0102 602/16 |

FOREIGN PATENT DOCUMENTS

| | | |
|---|---|---|
| CN | 2261237 Y | 9/1997 |
| CN | 201320231 Y | 10/2009 |
| CN | 102846417 A | 1/2013 |
| CN | 103860305 A | 6/2014 |
| DE | 35 08 844 A1 | 9/1986 |
| EP | 1 588 678 A1 | 10/2005 |
| JP | 2011-87926 A | 5/2011 |

OTHER PUBLICATIONS

Chinese First Examination Report and Search Report of corresponding China patent Application No. 201410086136.9, dated Oct. 10, 2015.

* cited by examiner

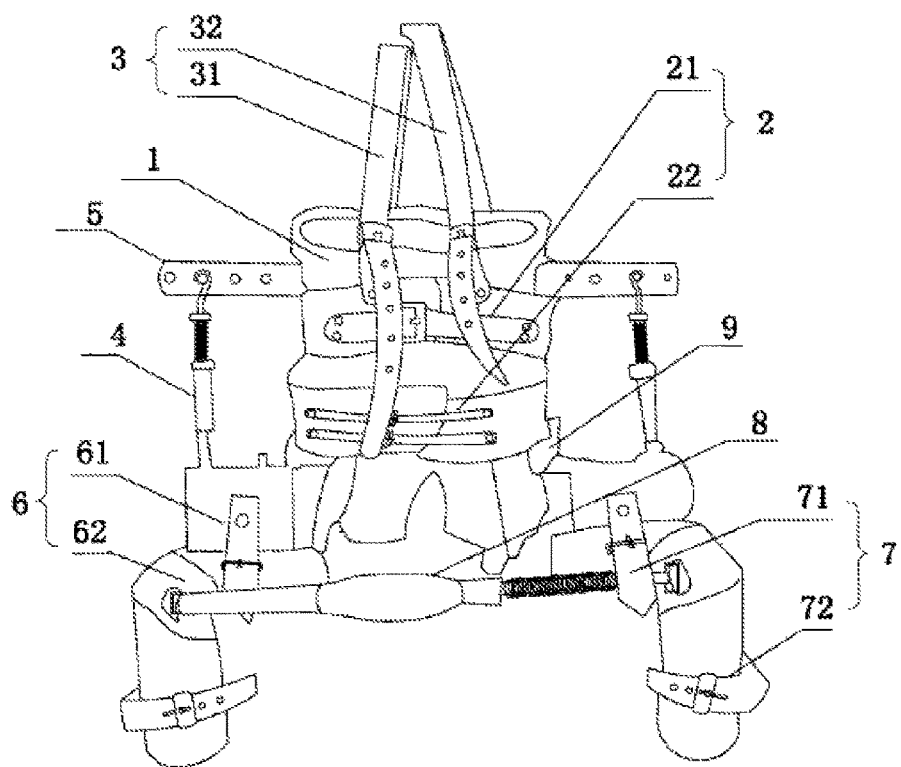

THERAPEUTIC DEVICE FOR SLOWLY STRETCHING THREE-DIMENSIONAL HIP JOINT FOR REPOSITION MOVEMENT

CROSS-REFERENCE TO RELATED APPLICATIONS

This application is a continuation of International Application No. PCT/CN2015/000162, filed on Mar. 10, 2015, which claims the priority benefit of China Patent Application No. 201410086136.9, filed on Mar. 11, 2014. The contents of the above identified applications are incorporated herein by reference in their entireties.

TECHNICAL FIELD

The present invention relates to the field of medical devices and, in particular, to a therapeutic device for slowly stretching a three-dimensional hip joint for reposition movement.

BACKGROUND

A classical treatment method for developmental dysplasia of the hip (DDH) is that if a child diagnosed with the developmental dysplasia of the hip is under 3 years old, it will needs to perform, under anesthesia, a manual reposition to put the hip joint back to a normal position, i.e. to perform a closed reduction, if successful, it needs a special gypsum (frog gypsum) so as to ensure that the hip joint is in a correct position. An overall treatment time by wearing the frog gypsum is nine months. The gypsum needs to be replaced under anesthesia every three months, total of three times, in order to adapt to the growth of child and ensure hardness of the gypsum, since as wearing time prolongs, the gypsum may become soft. The gypsum needs to be worn till the hip joint is restored to a normal position, nearly one year, then it can be removed. After the gypsum is removed, a special brace and physical therapy are required to enable muscles of hips and legs to recover gradually, and thus a travelling function is restored gradually.

The classical treatment method has the following disadvantages: repetitive anesthesia for more than three times, repetitive reduction and gypsum fixation; stiffness due to long term fixation, arrested development and developmental imbalance of the hip system; mal-development of concentric circles of the femoral head, and poor maintenance of stability of the hip joint.

SUMMARY

An object of the present invention is to provide a therapeutic device for slowly stretching a three-dimensional hip joint for reposition movement, which aims at solving problems in the classical treatment method, such as request for repetitive anesthesia, repetitive reduction and gypsum fixation, stiffness due to long term fixation, arrested development and developmental imbalance of the hip system, mal-development of concentric circles of the femoral head, and poor maintenance of stability of the hip joint.

The object of the present invention is achieved by a therapeutic device for slowly stretching a three-dimensional hip joint for reposition movement, including: a square-shaped back cover comprising left and right ends and upper and lower ends adjacent to the left and right ends, a chest-abdomen fastener fixing band, a shoulder fastener suspension band, upward-downward lifting chute screws, a pair of wing-shaped supporting bars with hooks evenly provided on surfaces thereof, a pair of limb fixing bars, limb fastener fixing bands, an inward-outward telescopic screw and a pair of hip joint forward-backward movement adjusters; wherein, both ends of the chest-abdomen fastener fixing band are fixed to the left and right ends of the back cover respectively; one end of the shoulder fastener suspension band is fixed to the upper end of the back cover, and the other end of the shoulder fastener suspension band is fixed to the chest-abdomen fastener fixing band; one end of one of the pair of wing-shaped supporting bars is fixed to the left end of the back cover, the other end thereof extends far away from the back cover, and one end of the other of the pair of wing-shaped supporting bars is fixed to the right end of the back cover, the other end thereof extends far away from the back cover; one end of each of the pair of limb fixing bars is connected to a corresponding telescopic end of each of the pair of hip joint forward-backward movement adjusters, and the other two ends of the pair of hip joint forward-backward movement adjusters are fixed to the left and right ends of the back cover respectively; and connection points between the pair of hip joint forward-backward movement adjusters and the back cover are below the chest-abdomen fastener fixing band;

one end of each of the upward-downward lifting chute screws is connected to a hook of a corresponding wing-shaped supporting bar, and the other end is connected to a corresponding limb fixing bar that is at the same side as the corresponding wing-shaped supporting bar; and both ends of the inward-outward telescopic screw are connected between the pair of limb fixing bars which are provided with the limb fastener fixing bands.

Preferably, each of the pair of limb fixing bars includes a first section limb fixing bar in parallel with the wing-shaped supporting bars and a second section limb fixing bar perpendicular to the first section limb fixing bar; each of the limb fastener fixing bands includes an upper limb fastener fixing band and a lower limb fastener fixing band; wherein, both the back cover and the upward-downward lifting chute screws are directly connected to the first section limb fixing bars of the pair of limb fixing bars, and the first section limb fixing bars are provided with the upper limb fastener fixing bands;

the second section limb fixing bars are provided with the lower limb fastener fixing bands; and both ends of the inward-outward telescopic screw are connected to the corresponding two second section limb fixing bars of the pair of limb fixing bars respectively.

Preferably, the first section limb fixing bars are formed by a rigid material, and the second section limb fixing bars are formed by a plastic foam material.

Preferably, the chest-abdomen fastener fixing band includes a chest fastener fixing band and an abdomen fastener fixing band; both ends of the chest fastener fixing band are fixed to the left and right ends of the back cover respectively; the abdomen fastener fixing band is right below the chest fastener fixing band, and both ends of the abdomen fastener fixing band are fixed to the left and right ends of the back cover respectively; one end of the shoulder fastener suspension band is fixed to the upper end of the back cover, and the other end of the shoulder fastener suspension band is fixed to the abdomen fastener fixing band; and connection points between the limb fixing bars and the back cover are below the abdomen fastener fixing band.

Preferably, the shoulder fastener suspension band includes a first shoulder fastener suspension band and a second shoulder fastener suspension band; where connection points between the first shoulder fastener suspension band and the back cover and between the first shoulder fastener suspension band and the abdomen fastener fixing band are close to the left end of the back cover; and connection points between the second shoulder fastener suspension band and the back cover and between the second shoulder fastener suspension band and the abdomen fastener fixing band are close to the right end of the back cover.

Preferably, the back cover is formed by a rigid material, and the back cover has a shape that is adapted to a human back shape; the back cover is provided with a sponge layer at a side against human back.

Preferably, the inward-outward telescopic screw is provided with graduations.

Preferably, the upward-downward lifting chute screws are provided with graduations.

In comparison with the disadvantages and deficiencies in the prior art, the present invention has the following beneficial effects:

(1) The present invention not only allows the developmental dysplasia of the hip to get good reposition therapy, but also avoids pains from the classical treatment method such as repetitive anesthesia, repetitive manipulative reduction and gypsum fixation, and also avoids arrested development of the hip system caused by imbalance state of soft tissues around the hip joint due to long term soft and dormant, as well as severe gypsum syndromes such as stiffness due to long term fixation of the joint resulting from repetitive reposition and fixation by the gypsum.

(2) The therapeutic device according to the present invention is convenient to use, comfortable to wear, easy to manufacture due to simple structure, economical and durable.

BRIEF DESCRIPTION OF DRAWINGS

FIG. 1 is a schematic structural diagram of a therapeutic device for slowly stretching a three-dimensional hip joint for reposition movement according to an embodiment of the present invention.

DESCRIPTION OF EMBODIMENTS

In order to make objects, technical solutions and advantages of the present invention clearer, the present invention will be described hereunder in details with reference to accompanying drawings and embodiments. It should be understood that, specific embodiments described herein are merely intended for illustrating the present invention, rather than limiting the present invention.

Reference may be made to FIG. 1, which is a schematic structural diagram of a therapeutic device for slowly stretching a three-dimensional hip joint for reposition movement according to an embodiment of the present invention.

A therapeutic device for slowly stretching a three-dimensional hip joint for reposition movement includes: a square-shaped back cover 1 comprising left and right ends and upper and lower ends adjacent to the left and right ends, a chest-abdomen fastener fixing band 2, a shoulder fastener suspension band 3, upward-downward lifting chute screws 4, a pair of wing-shaped supporting bars 5 with hooks evenly provided on surfaces thereof, a pair of limb fixing bars 6, limb fastener fixing bands 7, an inward-outward telescopic screw 8 and a pair of hip joint forward-backward movement adjusters 9; wherein both ends of the chest-abdomen fastener fixing band 2 are fixed to left and right ends of the back cover 1 respectively; one end of the shoulder fastener suspension band 3 is fixed to the upper end of the back cover 1, and the other end of the shoulder fastener suspension band 3 is fixed to the chest-abdomen fastener fixing band 2; one end of one of the pair of wing-shaped supporting bars 5 is fixed to the left end of the back cover 1, and the other end thereof extends far away from the back cover 1, and one end of the other of the pair of wing-shaped supporting bars 5 is fixed to the right end of the back cover 1, the other end thereof extends far away from the back cover 1; one end of each of the pair of limb fixing bars 6 is connected to a corresponding telescopic end of each of the pair of hip joint forward-backward movement adjusters 9, and the other two ends of the pair of hip joint forward-backward movement adjusters 9 are fixed to the left and right ends of the back cover 1 respectively; and connection points between the pair of hip joint forward-backward movement adjusters 9 and the back cover 1 are below the chest-abdomen fastener fixing band 2.

One end of each of the upward-downward lifting chute screws 4 is connected to a hook of a corresponding wing-shaped supporting bar 5, and the other end is connected to a corresponding limb fixing bars 6 that is at the same side as the corresponding wing-shaped supporting bar 5; and both ends of the inward-outward telescopic screw 8 are connected between the pair of limb fixing bars 6 which are provided with the limb fastener fixing bands 7.

More specifically, in order to make patients more comfortable when wearing, in an embodiment of the present invention, the chest-abdomen fastener fixing band 2 includes a chest fastener fixing band 21 and an abdomen fastener fixing band 22; both ends of the chest fastener fixing band 21 are fixed to the left and right ends of the back cover 1 respectively; the abdomen fastener fixing band 22 is right below the chest fastener fixing band 21, and both ends of the abdomen fastener fixing band 22 are fixed to the left and right ends of the back cover 1 respectively; one end of the shoulder fastener suspension band 3 is fixed to the upper end of the back cover 1, and the other end of the shoulder fastener suspension band 3 is fixed to the abdomen fastener fixing band 22; and connection points between the limb fixing bars 6 and the back cover 1 are below the abdomen fastener fixing band 22.

More specifically, in order to make patients more comfortable when the wearing, in an embodiment of the present invention, the back cover 1 is formed by a rigid material, and the back cover 1 has a shape that is adapted to a human back shape; and the back cover 1 is provided with a sponge layer at a side against human back.

More specifically, in order to make patients more comfortable when wearing, in an embodiment of the present invention, the shoulder fastener suspension band 3 includes a first shoulder fastener suspension band 31 and a second shoulder fastener suspension band 32; where connection points between the first shoulder fastener suspension band 31 and the back cover 1 and between the first shoulder fastener suspension band 31 and the abdomen fastener fixing band 22 are close to the left end of the back cover 1; and connection points between the second shoulder fastener suspension band 32 and the back cover 1 and between the second shoulder fastener suspension band 32 and the abdomen fastener fixing band 22 are close to the right end of the back cover 1.

More specifically, in order to allow the doctor to more accurately bring the femoral head into the acetabulum and conduct a reposition operation, in an embodiment of the present invention, both the inward-outward telescopic screw 8 and the upward-downward lifting chute screws 4 are provided with graduations.

In an embodiment of the present invention, during practical use, the back cover 1 is wore by a patient on his back, the first shoulder fastener suspension band 31 and the second shoulder fastener suspension band 32 lay on shoulders of the patient respectively, the chest fastener fixing band 21 and the abdomen fastener fixing band 22 are tightly buckled to the patient's chest and abdomen, the pair of limb fixing bars 6 are rested on left and right thighs of the patient respectively and are locked by the limb fastener fixing bands 7; the upward-downward lifting chute screws 4 may be used for adjustment according to body length of the patient, and the hip joint forward-backward movement adjusters 9 (the hip joint forward-backward movement adjusters 9 may have the same structure as the inward-outward telescopic screw 8) may be used for adjustment according to leg length of the patient. When wearing, the patent is required to bend his hip joints of both limbs by a degree of 45°-70°, bend and abduct his knees by a degree of 45°-70°, and then fix the device. Under the guidance of a doctor, a reset screw of the inward-outward telescopic screw 8 is tightened every day for slowly stretching according to the maximum tolerance capacity and soft tissue stretch stress of the patient, and the inward-outward telescopic screw 8 will be tightened to elongate or shorten 2 mm, for every circle that the reset screw is tightened. The inward-outward telescopic screw 8 is tightened to elongate or shorten 1-2 cm every day, without the need to cut off the adductor, and when the hip joint is bent by 90°, and is abducted by 90°, reposition by slowly stretching may be substantially completed, and an imaging examination may then be performed for verification (color ultrasonic inspection, X-ray or roentgenoscopy). If the reposition fails, when the femoral head has not been received into the acetabulum, a three-dimensional planar angle adjustment may be slowly performed under the imaging inspection to accurately receive the femoral head into the acetabulum, and after the reposition succeeds, the reset screw is tightened to fix the therapeutic device for slowly stretching a three-dimensional hip joint for reposition movement onto the patent's body, and then perform an imaging review.

In the present invention, according to Harris' law, that is, femoral head and acetabulum being concentric is a basic condition for hip development, reposition and fixation for the developmental dysplasia of the hip (DDH) without anesthesia is just like a "frog position" reposition method of hip joint of an adult bull, adopted in Kazakh Medical Therapy, and by slow dynamic adjustment, reposition and fixation for the patient under a "frog position" condition, fixation effect is reliable, stable, comfortable for patient, convenient and easy for urine and feces management, and also the hip joint can maintain proper activities, under maintenance of the "device", as a result, the therapy for hip joint in motion status promotes blood circulation of the femoral head, and development ratio of femoral head and acetabulum are suitable under the therapy for the hip joint in motion status. When the reposition therapy has been maintained for three months, and articular capsule and round ligament of the femoral head are almost retracted to normal, bending and abduction angles of the hip joint are regulated gradually. The bending angle of 90° and the abduction angle of 90° of the hip joint are all reduced to 70°. After six months of motion therapy, the bending angle and the abduction angle of 70° of the hip joint are then adjusted dynamically and gradually to 54° and 45° respectively, and the patient starts to stand and move with his hand on the wall in a progressive manner. After nine months of motion therapy, dislocation will not occur any more after the "device" is removed.

The present invention not only allows the developmental dysplasia of the hip to get good reposition therapy, but also avoids pains from the classical treatment method such as repetitive anesthesia, repetitive manipulative reduction and gypsum fixation, and also avoids arrested development of the hip system caused by imbalance state of soft tissues around the hip joint due to long term soft and dormant, as well as severe gypsum syndromes such as stiffness due to long term fixation of the joint resulting from repetitive reposition and fixation by the gypsum. If development ratio of femoral head and acetabulum of the hip joint is imbalanced, then stability of the hip joint cannot be maintained, even the treatment will fail. This disease should be early diagnosed and early treated. The earlier the treatment, the better the effect; the older the age, the worse the effect.

In a further process of implementation, in order to make the device of the present invention more suitable for human structure and use, in an embodiment of the present invention, each of the limb fixing bars 6 includes a first section limb fixing bar 61 in parallel with the wing-shaped supporting bars 5 and a second section limb fixing bar 62 perpendicular to the first section limb fixing bar 61; each of the limb fastener fixing bands 7 includes an upper limb fastener fixing band 71 and a lower limb fastener fixing band 72; wherein both the back cover 1 and the upward-downward lifting chute screws 4 are directly connected to the first section limb fixing bars 61, and the first section limb fixing bars 61 are provided with the upper limb fastener fixing bands 71;

the second section limb fixing bars 62 are provided with the lower limb fastener fixing bands 72; and both ends of the inward-outward telescopic screw 8 are connected to the corresponding two second section limb fixing bars 62 respectively.

More specifically, in order to allow the entire structure of the present device to be more stable, the body part of the device to be connected to the patient's limb parts more securely and to make it more comfortable for the patient to wear, in an embodiment of the present invention, the first section limb fixing bars 61 are formed by a rigid material, and the second section limb fixing bars 62 are formed by a plastic foam material.

In an embodiment of the present invention, during practical use, thighs of the patient are fixed to the first section limb fixing bars 61 via the upper limb fastener fixing bands 71, and shanks thereof are fixed to the second section limb fixing bars 62 via the lower limb fastener fixing bands 72, and since the first section limb fixing bars 61 are perpendicular to the second section limb fixing bars 62, which more tallies with human's leg structure and force bearing mode, when the inward-outward telescopic screw 8 is adjusted, forces transferred from the first section limb fixing bars 61 to the second section limb fixing bars 62 are more stable. Furthermore, the first section limb fixing bars 61 are formed by a relatively rigid material, capable of well withstanding the impact force brought by the body part, i.e., the back cover 1, the therapeutic device of the present invention is thus more economical and durable.

The foregoing is merely preferred embodiments of the present invention, and should not be considered as a limitation to the present invention. Any amendment, equivalent replacement, and improvement made within the spirit and principle of the present invention shall fall within the protection scope of the present invention.

What is claimed is:

1. A therapeutic device for slowly stretching a three-dimensional hip joint for reposition movement, comprising: a square-shaped back cover comprising left and right ends and upper and lower ends adjacent to the left and right ends, a chest-abdomen fastener fixing band, a shoulder fastener suspension band, upward-downward lifting chute screws, a pair of wing-shaped supporting bars with hooks evenly provided on surfaces thereof, a pair of limb fixing bars, limb fastener fixing bands, an inward-outward telescopic screw and a pair of hip joint forward-backward movement adjusters; wherein, > both ends of the chest-abdomen fastener fixing band are fixed to the left and right ends of the back cover respectively; one end of the shoulder fastener suspension band is fixed to the upper end of the back cover, and the other end of the shoulder fastener suspension band is fixed to the chest-abdomen fastener fixing band; one end of one of the pair of wing-shaped supporting bars is fixed to the left end of the back cover, the other end thereof extends far away from the back cover, and one end of the other of the pair of wing-shaped supporting bars is fixed to the right end of the back cover, the other end thereof extends far away from the back cover; one end of each of the pair of limb fixing bars is connected to a corresponding telescopic end of each of the pair of hip joint forward-backward movement adjusters, and the other two ends of the pair of hip joint forward-backward movement adjusters are fixed to the left and right ends of the back cover respectively; and connection points between the pair of hip joint forward-backward movement adjusters and the back cover are below the chest-abdomen fastener fixing band; and
>
> one end of each of the upward-downward lifting chute screws is connected to a hook of a corresponding wing-shaped supporting bar, and the other end is connected to a corresponding limb fixing bar that is at the same side as the corresponding wing-shaped supporting bar; and both ends of the inward-outward telescopic screw are connected between the pair of limb fixing bars which are provided with the limb fastener fixing bands.

2. The therapeutic device for slowly stretching a three-dimensional hip joint for reposition movement according to claim 1, wherein each of the pair of the limb fixing bars includes a first section limb fixing bar in parallel with the wing-shaped supporting bars and a second section limb fixing bar perpendicular to the first section limb fixing bar; each of the limb fastener fixing bands includes an upper limb fastener fixing band and a lower limb fastener fixing band; wherein, > both the back cover and the upward-downward lifting chute screws are directly connected to the first section limb fixing bars of the pair of limb fixing bars, and the first section limb fixing bars are provided with the upper limb fastener fixing bands; and
>
> the second section limb fixing bars are provided with the lower limb fastener fixing bands; and both ends of the inward-outward telescopic screw are connected to the corresponding two second section limb fixing bars of the pair of limb fixing bars respectively.

3. The therapeutic device for slowly stretching a three-dimensional hip joint for reposition movement according to claim 2, wherein the first section limb fixing bars are formed by a rigid material, and the second section limb fixing bars are formed by a plastic foam material.

4. The therapeutic device for slowly stretching a three-dimensional hip joint for reposition movement according to claim 1, wherein the chest-abdomen fastener fixing band includes a chest fastener fixing band and an abdomen fastener fixing band; both ends of the chest fastener fixing band are fixed to the left and right ends of the back cover respectively; the abdomen fastener fixing band is right below the chest fastener fixing band, and both ends of the abdomen fastener fixing band are fixed to the left and right ends of the back cover respectively; one end of the shoulder fastener suspension band is fixed to the upper end of the back cover, and the other end of the shoulder fastener suspension band is fixed to the abdomen fastener fixing band; and > connection points between the limb fixing bars and the back cover are below the abdomen fastener fixing band.

5. The therapeutic device for slowly stretching a three-dimensional hip joint for reposition movement according to claim 4, wherein the shoulder fastener suspension band includes a first shoulder fastener suspension band and a second shoulder fastener suspension band; wherein > connection points between the first shoulder fastener suspension band and the back cover and between the first shoulder fastener suspension band and the abdomen fastener fixing band are close to the left end of the back cover; and connection points between the second shoulder fastener suspension band and the back cover and between the second shoulder fastener suspension band and the abdomen fastener fixing band are close to the right end of the back cover.

6. The therapeutic device for slowly stretching a three-dimensional hip joint for reposition movement according to claim 5, wherein the back cover is formed by a rigid material, and the back cover has a shape that is adapted to a human back shape; the back cover is provided with a sponge layer at a side against human back.

7. The therapeutic device for slowly stretching a three-dimensional hip joint for reposition movement according to claim 6, wherein the inward-outward telescopic screw is provided with graduations.

8. The therapeutic device for slowly stretching a three-dimensional hip joint for reposition movement according to claim 7, wherein the upward-downward lifting chute screws are provided with graduations.

* * * * *